(12) United States Patent
Khare et al.

(10) Patent No.: US 7,916,828 B1
(45) Date of Patent: Mar. 29, 2011

(54) METHOD FOR IMAGE CONSTRUCTION

(75) Inventors: Kedar Bhalachandra Khare, Niskayuna, NY (US); Bernhard Erich Hermann Claus, Niskayuna, NY (US); Jeffrey Wayne Eberhard, Albany, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 12/683,345

(22) Filed: Jan. 6, 2010

(51) Int. Cl.
*A61B 6/00* (2006.01)
(52) U.S. Cl. .......................................................... 378/4
(58) Field of Classification Search ......... 378/4; 382/131
See application file for complete search history.

(56) References Cited

U.S. PATENT DOCUMENTS

| | | | | |
|---|---|---|---|---|
| 5,053,958 A | * | 10/1991 | Tam | 378/4 |
| 5,473,655 A | * | 12/1995 | Hu | 378/4 |
| 5,933,471 A | * | 8/1999 | Kalvin | 378/4 |
| 6,766,048 B1 | * | 7/2004 | Launay et al. | 382/154 |
| 6,788,758 B2 | * | 9/2004 | De Villiers | 378/4 |
| 6,845,143 B2 | * | 1/2005 | Gringauz et al. | 378/8 |
| 6,862,335 B2 | * | 3/2005 | Basu et al. | 378/4 |
| 6,901,132 B2 | | 5/2005 | Eberhard et al. | |
| 7,362,843 B2 | * | 4/2008 | Basu et al. | 382/131 |
| 7,428,292 B2 | | 9/2008 | De Man et al. | |
| 2002/0006216 A1 | * | 1/2002 | Armato et al. | 382/131 |
| 2005/0018902 A1 | * | 1/2005 | Liang | 382/154 |
| 2005/0207628 A1 | * | 9/2005 | Kim | 382/128 |
| 2009/0175523 A1 | * | 7/2009 | Chen et al. | 382/130 |
| 2009/0262996 A1 | * | 10/2009 | Samsonov et al. | 382/130 |

OTHER PUBLICATIONS

Yu et al., Compressed sensing based interior tomography, Phys Med Biol, 54, 2009, pp. 2791-2805.*
Nett et al., Tomosynthesis via total variation minimization reconstruction and prior image constrained compressed sensing (PICCS) on a C-arm system, NIH Public Acces, Pro Soc Photo Opt Instrum Eng., Mar. 2008, pp. 1-14.*
Chen et al., Prior image constrained compressed sensing (PICCS): A method to accurately reconstruct dynamic CT images from highly undersampled projection data sets, Med Phys, Feb. 2008, pp. 1-8.*

\* cited by examiner

*Primary Examiner* — Edward J Glick
*Assistant Examiner* — Alexander H Taningco
(74) *Attorney, Agent, or Firm* — Joseph J. Christian

(57) ABSTRACT

In one embodiment, a method of tomographic image construction includes performing sparsification on initial projection data for an object with a processor to provide sparsified projection data of the object. The method also includes back-projecting the sparsified projection data with the processor to provide a three-dimensional image of the object, and performing sparsification on the three-dimensional image with the processor to provide a sparsified image.

20 Claims, 2 Drawing Sheets

METHOD FOR IMAGE CONSTRUCTION

BACKGROUND OF THE INVENTION

The subject matter disclosed herein relates to a procedure for image construction based on data that is limited or incomplete.

Conventional imaging systems are utilized for a wide variety of purposes. For example, X-ray imaging systems are frequently utilized for medical, security, and manufacturing processes. Such systems may be employed to produce images that can be utilized for various decision-making procedures, such as medical diagnosis, threat detection, quality control, and so forth. However, proper decision-making may be negatively impacted by incomplete or distorted images. For example, conventional imaging systems often provide images with streaking artifacts, which can considerably degrade image quality for further utilization of the images in a decision-making process.

Tomography is an imaging technique that essentially images in sections or by sectioning. Tomography may include imaging by rotating or translating a radiation source and one or more associated detectors such that differing views of an object may be obtained. Alternately, the object to be imaged can be scanned past stationary source(s) and detector(s). As an example, X-ray tomography is an imaging method in which one or both of an X-ray tube and a detector are rotated or translated relative to a feature that is being imaged to obtain projection images of the feature from different angular positions. The projection images provided by the X-ray tube and detector from other angles may be utilized and combined to define a three-dimensional volume or otherwise provide a three-dimensional context. Such projection images may be referred to herein as views. It should be noted that it may be desirable to limit the number of views obtained by a particular imaging system to limit exposure to X-rays, limit expenses, and conserve time. For example, security systems such as airport baggage scanners may benefit from relatively rapid operation obtained by utilizing a limited number of views. However, it is now recognized that when a limited number of views are available image quality frequently suffers.

Conventional methods and systems for addressing image degradation such as that discussed above may be excessively expensive or overly time consuming for implementation in the desired areas of use. Accordingly, it is now recognized that it is desirable to provide an imaging system and procedure that reduces, eliminates, and/or reduces the impact of image distortions generated by limited numbers of views.

BRIEF DESCRIPTION OF THE INVENTION

In one embodiment, a method of tomographic image construction includes performing sparsification on initial projection data for an object with a processor to provide sparsified projection data of the object. The method also includes backprojecting the sparsified projection data with the processor to provide a three-dimensional image of the object, and performing sparsification on the three-dimensional image with the processor to provide a sparsified image.

In one embodiment, a tomographic imaging system includes a radiation source configured to emit radiation into an object, a radiation detector configured to detect the radiation after attenuation by the object to produce initial projection data of the object, a processor, and a memory. The memory is programmed with computer-readable code configured to perform sparsification on the initial projection data to provide sparsified projection data, backproject the sparsified projection data to provide a three-dimensional image, and perform sparsification on the three-dimensional image to provide a sparsified image of the object.

In one embodiment, a method of tomographic image construction using a programmed processor includes performing a first process of thresholding on initial projection data for an object at a threshold having a level to provide thresholded projection data of the object indicating high density components of the object. The method also includes backprojecting the thresholded projection data to provide a three-dimensional image of the object, and performing a second process of thresholding on the three-dimensional image to provide thresholded image data.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Present embodiments are directed to systems and methods for achieving quantitatively accurate tomographic image reconstruction with limited or minimal streaking and out-of-plane artifacts due to incomplete data. Present embodiments include or are configured to perform an image reconstruction method that is applicable to a wide variety of situations involving projection-based imaging with incomplete data. Methods in accordance with present embodiments can significantly improve image quality for a variety of projection-based systems, such as X-ray, Computed Tomography (CT), Position Emission Tomography (PET), Single Photon Emission Computed Tomography (SPECT), and so forth, which typically suffer from incomplete data artifacts in the images because such projection-based modalities may have insufficient projection data for complete image reconstruction. As discussed in further detail below, present embodiments utilize sparsification operations in both image and data domains to reduce or eliminate streaking artifacts that are often present in images when conventional linear algorithms (e.g., filtered backprojection and algebraic reconstruction) are used for image construction.

Specifically, present embodiments include systems and methods that perform sparsification in both image and data domains as part of an iterative process to provide quantitatively accurate image construction. Indeed, present embodiments may include systems and procedures for obtaining and performing sparsification on projection data for an object (e.g., a piece of luggage or a patient), backprojecting the sparsified projection data to reconstruct a three-dimensional or volumetric image of the object, and performing sparsification of the image to provide a sparsified image for evaluation. Further, embodiments include steps or features for converting the resulting image data into projection data, which is essentially projection data corresponding to the current estimate of the imaged object and may be referred to as reprojected projection data, proceeding with the iteration by eliminating the reprojected projection data from the original projection data, adjusting the sparsification and reinitiating the process in another iteration. The resulting sparsified image data from the various iterations may be combined to facilitate observation and analysis of the object. It should be noted that the initial sparsification step can be viewed as identifying dense material and subsequent adjustments of the sparsification may be to identify less dense material. The presently disclosed systems and methods are robust in that they are not sensitive to free parameters, and any individual choice of thresholding parameters is generally data-driven. Present embodiments are also generally computationally inexpensive with regard to solving iterative non-linear optimization problems with incomplete data.

Figure 1:
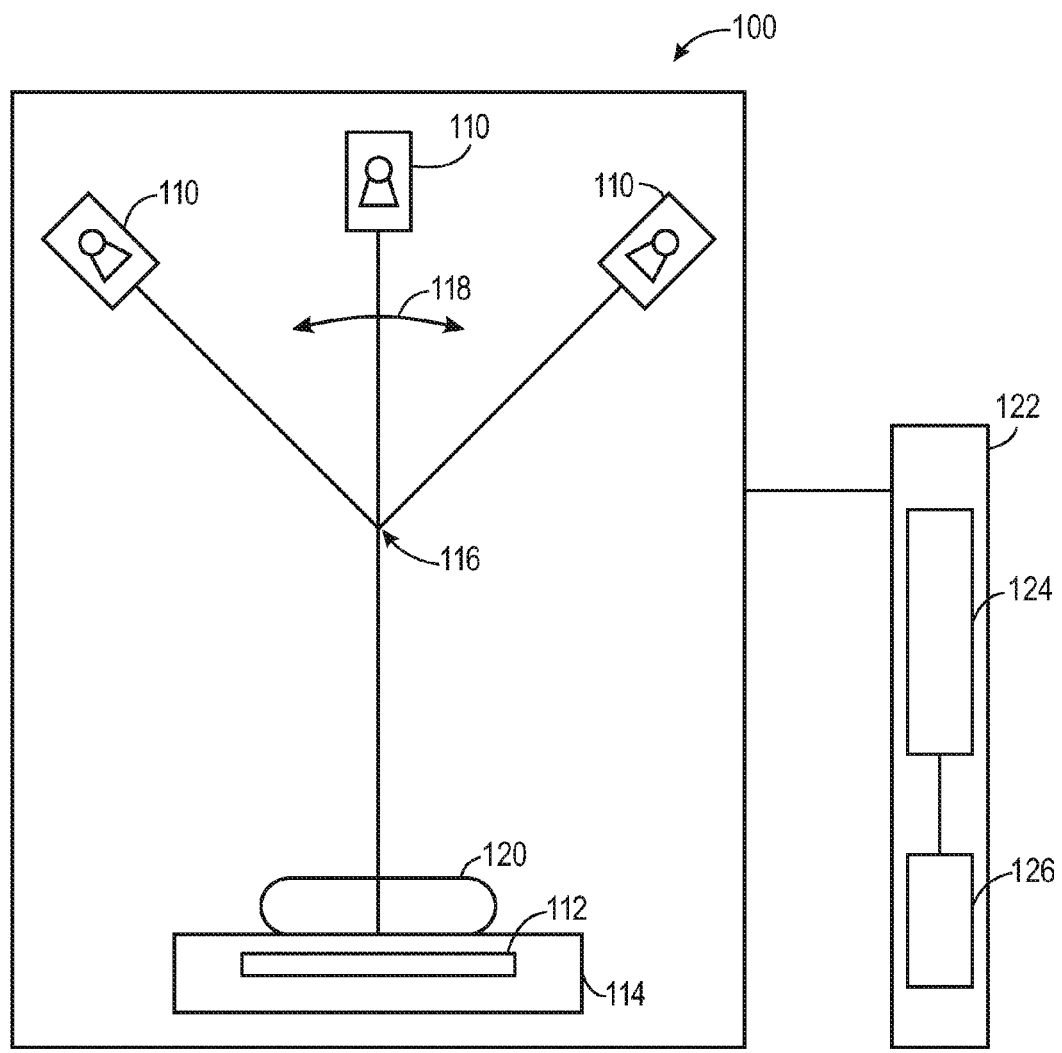
FIG. 1 is a schematic illustration of an embodiment of a front view of an imaging system 100 in accordance with the present disclosure.

FIG. 1 is a schematic illustration of a front view of an imaging system 100 in accordance with present embodiments. While some embodiments may include different functional aspects and equipment for different types of imaging, the system 100 in the illustrated embodiment includes an X-ray system with at least one X-ray source 110 and at least one X-ray detector 112 positioned within a housing 114 (e.g., a detector housing or image receptor). In some embodiments the X-ray source 110 and/or the X-ray detector 112 may be configured to rotate about an axis of rotation 116 and/or along an arc-shaped path 118 such that different projection data corresponding to different angles relative to an object 120 being observed or imaged can be obtained. In other embodiments, multiple X-ray sources and/or detectors may be employed in fixed and/or mobile arrangements to facilitate capturing projection data for different views. The system 100 also includes a computer 122 or a special purpose microprocessor, which controls the system 100 and performs certain functions in accordance with present embodiments. The computer 122 may include a processor 124 and a memory 126. In accordance with one embodiment of the present disclosure, the memory 126 (e.g., a memory chip) may store functional computer-readable code that coordinates with the processor 124 and other system components to obtain projection data, perform sparsification on the projection data, convert data from a projection data domain to an image domain and visa versa, perform sparsification on projection and/or image data, perform iterative procedures, and perform algorithms in accordance with present embodiments.

To produce a particular view of an object with an X-ray system, such as the system 100 depicted in FIG. 1, X-ray radiation is typically emitted into the object as a primary beam from an X-ray source (e.g., an X-ray tube located inside a housing), such as the source 110. As the primary beam passes through the object, it is attenuated. That is, some of the radiation from the primary beam is absorbed or deflected in a process known as attenuation. The radiographic density of a component of the object being imaged is directly related to its attenuation coefficient. Thus, the denser a feature is, the higher rate of attenuation that the feature will have. After the primary beam has been attenuated, the remnant of the primary beam, which may be referred to as the remnant beam, is received by a detector, such as the detector 112. In some embodiments, the remnant beam exposes an image receptor of the detector 112 to produce projection data. Specifically, in one example, portions of the image receptor that are exposed to the least attenuated radiation will be processed as having a large number of counts or X-ray photons, and those areas exposed to the most attenuated radiation will be processed as having a smaller number of counts or X-ray photons. The system 100 utilizes projection data obtained in this manner to initiate an iterative procedure to provide clear and distinct image data. In contrast to traditional tomographic imaging systems, present embodiments utilize a limited number of views to provide data without image degradation. It should also be noted that present embodiments may include preprocessing of projection data, which may include a negative log transform which maps from the count/raw data domain to the attenuation (or: line-integral of attenuation) domain.

Indeed, it is recognized that imaging systems such as those utilized for security (e.g., airport baggage scanning), medical evaluation (e.g., mammography), volumetric computed tomography, and so forth can suffer from issues with image clarity related to incomplete data or a limited number of views. Specifically, for example, incomplete data may cause conventional X-ray systems to provide images with streaking artifacts that considerably degrade the images and cause difficulty in evaluation of the images. It is currently recognized that, in the normal operation of conventional imaging systems, the number of data points measured in the form of X-ray attenuation projections is typically less than the number of voxels in the image to be reconstructed, wherein each voxel is essentially a three-dimensional pixel with intensity values. It should be noted that similar incomplete data problems have also been found to occur in other imaging modalities where data is in the form of projections, such as position emission tomography (PET), single photon emission computed tomography (SPECT), and so forth.

Image reconstruction based on X-ray attenuation projections and the like can be cast as a solution of a linear system of equations, where the number of equations is less than the number of variables. However, as set forth above, it is now recognized that images reconstructed with traditional systems and methods for addressing incomplete data issues, where data is measured in the form of projections or line integrals, generally result in images showing streaking artifacts. Such streaking artifacts considerably degrade image quality and limit the use of images in any related decision-making processes. For example, it may be difficult to identify objects within baggage at an airport security check or it may be difficult to diagnose medical issues because of artifacts in the available images. Similarly, it is now recognized that traditional systems may result in out-of-plane artifacts (a different manifestation of the streak artifacts), which manifest as reduced intensity copies of features at a particular (incorrect) image location, while such features would properly occur at a different location in the image.

Accordingly, present embodiments are directed to an iterative approach to image reconstruction with incomplete data, wherein sparsification is applied in both data and image domains. Sparsification may include thresholding, which may be described as a process of separating pixels for processing based on whether the intensity value of the pixel is above or below a specified threshold level. From a computational perspective, thresholding is relatively inexpensive, and the threshold value may be adjusted to focus on different densities such that a range of density values may be observed. Indeed, in accordance with present embodiments the threshold may be adjusted to slowly identify less and less dense features. For example, present embodiments may perform thresholding with a slowly changing (e.g., decreasing) threshold parameter in both image and data domains. In one embodiment, the sign of the data may be switched such that the process starts by addressing the least-attenuating structures and moves toward the most-attenuating structures. Additionally, more complex thresholding schemes may be implemented in accordance with present embodiments, wherein both low and high density structures are simultaneously observed. It should be noted that, in present embodiments, data may be changed relative to the original data throughout the reconstruction process. Indeed, it is now recognized that data consistency requirements between the original data and the reconstructed image may be limited to the end of the reconstruction process. Further, it is now recognized that any modification to the data, if gradually reduced with iterations, is acceptable as long as consistency of the actual data with the final image is achieved.

It should be noted that, in some embodiments, sparsification may include different or varying techniques for separating pixels for processing. For example, sparsification may include a segmentation technique wherein pixels are grouped according to relative positioning and intensity values. Specifically, for example, pixels having relatively similar intensity levels and that are adjacent to one another may be grouped into a cluster and treated as a unit.

Figure 2:
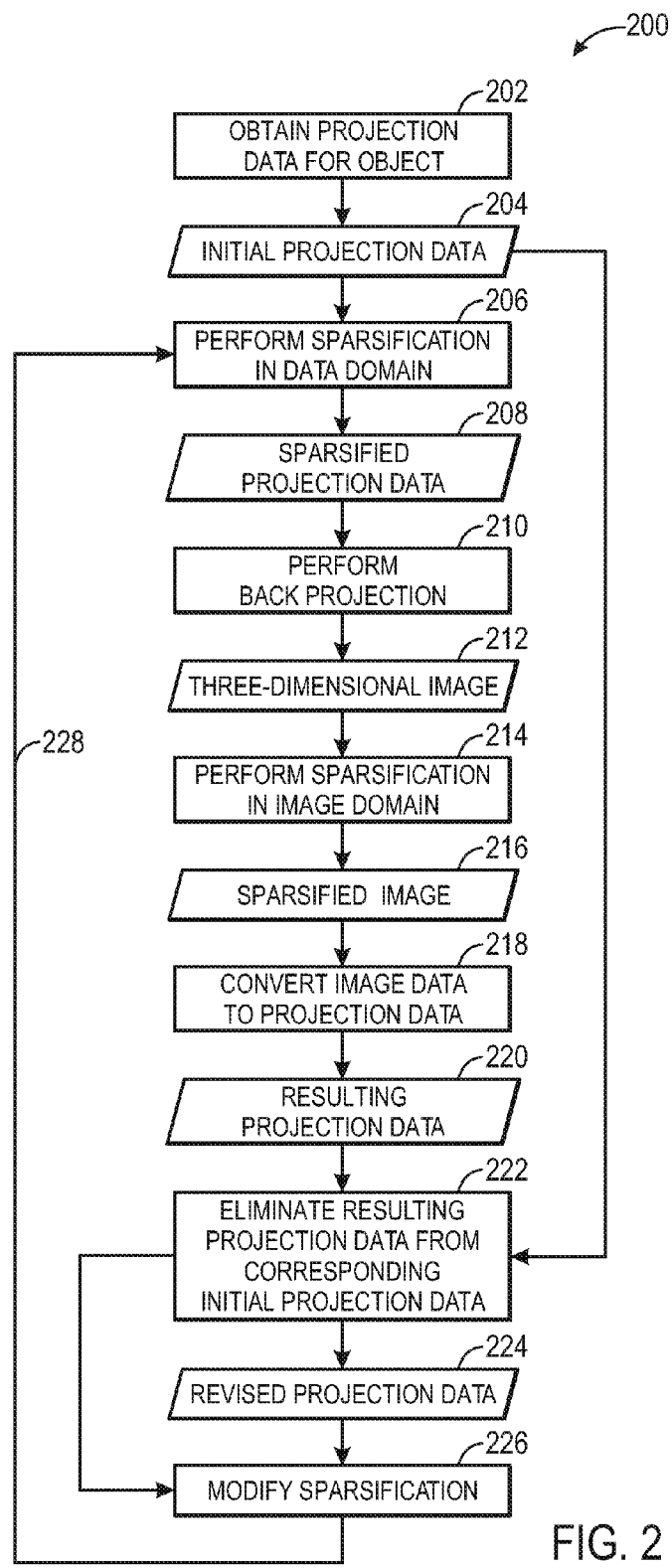
FIG. 2 is a process flow diagram of an embodiment of a method in accordance with the present disclosure.

FIG. 2 is a process flow diagram of a method in accordance with present embodiments. The method is generally indicated by reference numeral 200. The method 200 applies to reconstruction of volume images angularly undersampled projection data, i.e., from sub-Nyquist sampled projection data (e.g., analog signal data sampled at a rate lower than the Nyquist rate such that signal content is preserved without aliasing distortion). As indicated in FIG. 2, present embodiments may include or perform various iterative steps including conversion between projection and image domains in conjunction with sparsification to provide distinct images of an object being observed. More specifically, the method 200 includes an iterative image reconstruction procedure that utilizes relatively few (e.g., 100, 50, 40, 30, 25, 20, 16, 12, 10, or less) input projections to reconstruct a nearly artifact-free, quantitatively accurate three-dimensional image of an object, based on sparsification of either or both of the projection data and the three-dimensional image data at each iteration step. The iteration is configured such that large, high intensity objects are reconstructed first and smaller, low intensity objects are gradually added by varying the degree of sparsification (independently or in concert in the projection and image domains). In one embodiment, varying the degree of sparsification is achieved by approximately adjusting threshold levels. At the end of the method 200, the components of the object being evaluated are reconstructed and the measured data is used without modification (without sparsification). In one embodiment, sparsification includes thresholding, which is a very computationally efficient method of performing sparsification.

The method 200 begins with block 202, which generally represents obtaining projection data for an object, which may be referred to as initial projection data 204. This projection data includes a plurality of views of the object. For example, block 202 may represent capturing X-ray images for a number of different views by passing X-rays through the object from different angles relative to the object and exposing an X-ray detector using a system such as system 100. As represented by block 206, once the projection data has been obtained, it may be modified. More specifically, it may be utilized to perform sparsification (e.g., thresholding) in the projection or data domain to obtain sparsified projection data 208. Next, the sparsified projection data 208 is backprojected to reconstruct a three-dimensional image 210 of the object in an image domain, as represented by block 212. Once obtained, this reconstructed three-dimensional image 210 is also sparsified in accordance with present embodiments. Indeed, as represented by block 214, the three-dimensional image 210, which has been constructed from the sparsified projection data 208, is sparsified to produce a sparsified image 216. This may conclude a first iteration of the method 200.

The image domain information resulting from an iteration, which has been obtained as a result of the sparsification of both image and projection domains, includes substantially fewer streaking artifacts. However, depending on the level of sparsificaton, it will generally represent only a certain density level within the object being observed. Accordingly, resulting image data 216 can be reprojected (i.e., converted to the data domain), as illustrated by block 218, such that projection data 220 corresponding to the current estimate of the imaged object is obtained. Further, the resulting projections 220 (reprojected projection data) can be essentially subtracted out of the initial or original projection data 204, as represented by block 222, to obtain residual projection data 224. Next, as represented by block 226, the degree of sparsification may be modified (e.g., the threshold may be adjusted), and the procedure 200 can reinitiate another iteration with the residual projection data in place of the initial projection data, as represented by arrows 228, such that various density levels are observed. It should be noted that block 226 may represent both modification of the degree of sparsification in the projection domain and/or the image domain. Further, it should be noted that the sparsification parameters (e.g., threshold levels) may be different in the projection data and the image domain.

In one embodiment, the image data is updated by first backprojecting the residual projections such that a residual image is formed. Next, the residual image is added to the image data. Thus, in some embodiments, the various image datasets obtained through backprojection of the residuals may not be kept separate. However, keeping the various image datasets separate may be done in other embodiments. Further, in some embodiments, sparsification in the image domain can be performed on the backprojected residual, on the updated image, or both.

It should be noted that initial iterations may perform sparsification such that high density blocky objects are reconstructed. For example, threshold values may initially be set to a high level such that only very dense objects are indicated. As the iterations progress, sparsification may be reduced progressively in block 226 such that less dense objects are reconstructed after the information for the more dense items have been removed from the projections as discussed above. In some embodiments, the procedure represented by block 226 may include modifying the thresholds used in the image reconstruction process based on a statistical distribution of a current estimated image, the projection data, the current residual, or a combination of these in some transform basis (including the typical pixel basis representation). After a set number of iterations or when a certain level of consistency is reached, the completed image may be provided for analysis. Further, data consistency may be achieved at the end of the reconstruction As indicated above, image reconstruction for projection-based imaging can be set forth as a solution of a linear system of equations. For example, the image reconstruction problem may be represented by the following equation:

$$y=Af \qquad (1)$$

Here f represents the volume image of the object to be reconstructed, A represents the system matrix operator, which typically corresponds to the formation of line integrals of the image, and y represents the measured projection data. Embodiments of the present disclosure relate in particular to imaging situations in which the number of voxels in the image f is much larger than the number of measurements in the data vector y, making the system of equations in equation (1) an incomplete system. While there is no unique solution to such a system in general, present embodiments address this issue by employing sparsity transformations in both image and data domains. As set forth herein, "sparsity transformation" may refer to a representation of image/data in a transform domain where the number of coefficients needed to represent the image/data are less or much less (e.g., 10 to 100 times less) than the number of voxels/pixels respectively.

Such sparsity transformations exist since measured data or its image always has some spatial structure and is not completely arbitrary. Thus, the image and the data may be expressed as a sum of several elemental parts. For example, the following equation is representative:

$$y = \sum_i y_i, f = \sum_i f_i \quad (2)$$

where each of the components $y_i$ and $f_j$ have a sparse representation. In other words, the number of pixels or voxels in the data $y_i$ and image $f_j$ is much larger than the number of coefficients needed to represent them in some transform domain. Thus, $y_i$ and $f_j$ have a sparse representation. In accordance with present embodiments, the reconstruction problem is solved in an iterative manner such that each stage of the iterative solution involves solving a sparse problem:

$$y_i = Af_i \quad (3)$$

The sparsity constraint is typically imposed via an L1-norm constraint. Accordingly, at every stage in the iterative process, one solves an optimization problem:

$$\text{Minimize} \|y_i - Af_i\|_2 + \lambda \|Wf_i\|_i \quad (4)$$

Here, the first term is a data consistency term represented by squared error between the data and the forward projection of the solution. The second term represents the L1-norm which is the sum of the absolute values of the components of the vector:

$$\|h\|_1 = \sum_n |h_n| \quad (5)$$

where the symbol W represents a transformation or a combination of transformations in which the elemental image $f_j$ is sparse. The iterative procedure is typically stopped when the resultant image satisfies some constraint such as data consistency as represented by norm of error $\|y-Af\|$. In some embodiments, the iterative procedure may be halted upon reaching a designated number of iterations.

Present embodiments have been demonstrated to provide significant improvements in image quality with very few projections when applied to images of objects. While performance optimization is expected to depend on orientation of projections relative to the object being imaged, and to some extent on the nature of the object of interest, the basic method is directly applicable to medical imaging applications and non-destructive testing as well. Compared to traditional methods, present embodiments provide images wherein clutter/streaks and blurring are limited or minimized, energy is concentrated in the proper voxels, better localization of objects is achieved for appropriate slices, and quantitative accuracy is increased.

Technical effects in accordance with present embodiments include quantitatively accurate tomographic image reconstruction with limited or minimal streaking artifacts due to incomplete data. Present embodiments can significantly improve image quality for a variety of projection-based systems, such as X-ray, Computed Tomography (CT), Position Emission Tomography (PET), Single Photon Emission Computed Tomography (SPECT), and so forth, which typically suffer from incomplete data artifacts. The presently disclosed systems and methods are robust in that they are not sensitive to free parameters, and any individual choice of thresholding parameters is generally data-driven. Present embodiments are also generally computationally inexpensive with regard to solving iterative non-linear optimization problems with incomplete data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of tomographic image construction, comprising:
    performing sparsification on initial projection data for an object with a processor to provide sparsified projection data of the object;
    backprojecting the sparsified projection data with the processor to provide a three-dimensional image of the object; and
    performing sparsification on the three-dimensional image with the processor to provide a sparsified image.

2. The method of claim 1, comprising converting the sparsified image into reprojected projection data corresponding to the current estimate of the imaged object with the processor.

3. The method of claim 2, comprising eliminating the reprojected projection data from the initial projection data to provide residual projection data with the processor.

4. The method of claim 3, comprising adjusting a level of sparsification and repeating the method with the residual projection data as the initial projection data with the processor.

5. The method of claim 1, comprising providing a plurality of sparsified images based on a plurality of iterations with different levels of sparsification with the processor.

6. The method of claim 1, comprising providing a combination of a plurality of sparsified images based on a plurality of iterations with different levels of sparsification with the processor to provide an analysis image with the processor.

7. The method of claim 1, comprising obtaining initial projection data by emitting X-rays from an X-ray source into the object and detecting the X-rays after passing through and being attenuated by the object with an X-ray detector.

8. The method of claim 1, wherein sparsification comprises thresholding.

9. The method of claim 1, comprising modifying a threshold utilized in sparsification for each of a plurality of iterations with the processor based on a statistical distribution of a current estimate of the image, the initial projection data, a current residual, or a combination thereof.

10. The method of claim 1, comprising modifying a threshold utilized in sparsification for subsequent iterations based on a typical pixel basis representation with the processor.

11. A tomographic imaging system, comprising:
    a radiation source configured to emit radiation into an object;

a radiation detector configured to detect the radiation after attenuation by the object to produce initial projection data of the object;

a processor and a memory programmed with computer-readable code configured to:

perform sparsification on the initial projection data to provide sparsified projection data;

backproject the sparsified projection data to provide a three-dimensional image; and perform sparsification on the three-dimensional image to provide a sparsified image of the object.

12. The system of claim 11, wherein the memory is programmed to convert the sparsified image into reprojected projection data corresponding to the initial projection data.

13. The system of claim 12, wherein the memory is programmed to eliminate the reprojected projection data from the initial projection data to provide residual projection data.

14. The system of claim 13, wherein the memory is programmed to adjust a level of sparsification and reinitiate performing sparsification on the residual projection data.

15. The system of claim 11, wherein the memory is programmed to provide a plurality of sparsified images based on a plurality of iterations with different levels of sparsification.

16. The method of claim 15, wherein the memory is programmed to combine the plurality of sparsified images to provide an analysis image.

17. A method of tomographic image construction using a programmed processor, comprising:

performing a first process of thresholding on initial projection data for an object at a threshold having a level to provide thresholded projection data of the object indicating high density components of the object;

backprojecting the thresholded projection data to provide a three-dimensional image of the object; and performing a second process of thresholding on the three-dimensional image to provide thresholded image data.

18. The method of claim 17, comprising converting the thresholded image data into reprojected projection data corresponding to the initial projection data.

19. The method of claim 18, comprising eliminating the reprojected projection data from the initial projection data to provide residual projection data.

20. The method of claim 19, comprising adjusting the level of the threshold and repeating the method with the residual projection data as the initial projection data.

* * * * *

UNITED STATES PATENT AND TRADEMARK OFFICE
CERTIFICATE OF CORRECTION

| | | |
|---|---|---|
| PATENT NO. | : 7,916,828 B1 | Page 1 of 1 |
| APPLICATION NO. | : 12/683345 | |
| DATED | : March 29, 2011 | |
| INVENTOR(S) | : Khare et al. | |

It is certified that error appears in the above-identified patent and that said Letters Patent is hereby corrected as shown below:

In Column 7, Line 17, delete "$f_j$" and insert -- $f_i$ --, therefor.

In Column 7, Line 19, delete "$f_j$" and insert -- $f_i$ --, therefor.

In Column 7, Line 21, delete "$f_j$" and insert -- $f_i$ --, therefor.

In Column 7, Line 43, delete "$f_j$" and insert -- $f_i$ --, therefor.

Signed and Sealed this
Twenty-eighth Day of February, 2012

David J. Kappos
*Director of the United States Patent and Trademark Office*